(12) United States Patent
Folestad et al.

(10) Patent No.: US 7,329,430 B2
(45) Date of Patent: Feb. 12, 2008

(54) METHOD AND DEVICE FOR COATING PHARMACEUTICAL PRODUCTS

(75) Inventors: Staffan Folestad, Mölndal (SE); Ingela Niklasson Björn, Mölndal (SE); Daniel Ström, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 22 days.

(21) Appl. No.: 10/483,139

(22) PCT Filed: Jul. 9, 2002

(86) PCT No.: PCT/GB02/03143

§ 371 (c)(1), (2), (4) Date: Jul. 21, 2004

(87) PCT Pub. No.: WO03/006177

PCT Pub. Date: Jan. 23, 2003

(65) Prior Publication Data

US 2004/0247776 A1    Dec. 9, 2004

(30) Foreign Application Priority Data

Jul. 12, 2001 (SE) .................................. 0102511

(51) Int. Cl.
    *B05D 1/02* (2006.01)
(52) U.S. Cl. .................. 427/2.14; 427/2.15
(58) Field of Classification Search ............. None
    See application file for complete search history.

(56) References Cited

U.S. PATENT DOCUMENTS

| | | | |
|---|---|---|---|
| 3,790,079 A | | 2/1974 | Berglund et al. |
| 4,322,449 A | * | 3/1982 | Voss et al. .............. 427/2.14 |
| RE31,764 E | * | 12/1984 | Voss et al. .............. 427/2.14 |
| 4,568,559 A | * | 2/1986 | Nuwayser et al. ......... 427/2.15 |
| 5,158,804 A | * | 10/1992 | Alkan et al. .............. 427/213 |
| 5,589,225 A | | 12/1996 | Yamada et al. |

(Continued)

FOREIGN PATENT DOCUMENTS

DE    195 28 584 A1    2/1997

(Continued)

OTHER PUBLICATIONS

Andersson et al, Anal. Chem. 72, pp. 2099-2108, 2000.*

(Continued)

*Primary Examiner*—Erma Cameron
(74) *Attorney, Agent, or Firm*—Fish & Richardson P.C.

(57) ABSTRACT

The present invention relates to a method for coating of a pharmaceutical product. The method comprises the step of producing discrete droplets (7) of controlled size, shape and composition with at least one micro dispenser (1) and distributing droplets (7) with controlled velocity, time of flight. Also, the method comprises the step of controlling the production frequency and modulation of the droplets (7). Further, the method comprises the step of controlling the flow rate, temperature and composition of the carrier gas and directing droplets (7) towards particles (10) subjected to coating. The present invention also relates to a device for coating of a pharmaceutical product. The device comprises a droplet producing unit (1) and a droplet-directing unit (8). The droplet producing unit (1) is a piezo-actuated micro dispenser (1) for producing discrete droplets (7) and controlling the size, shape and composition of said droplets (7).

24 Claims, 4 Drawing Sheets

U.S. PATENT DOCUMENTS

Figure 1:
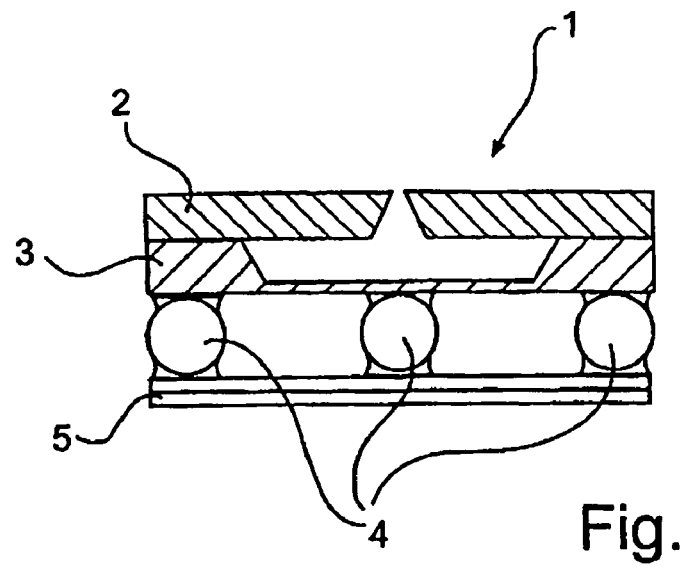
Figure 2:
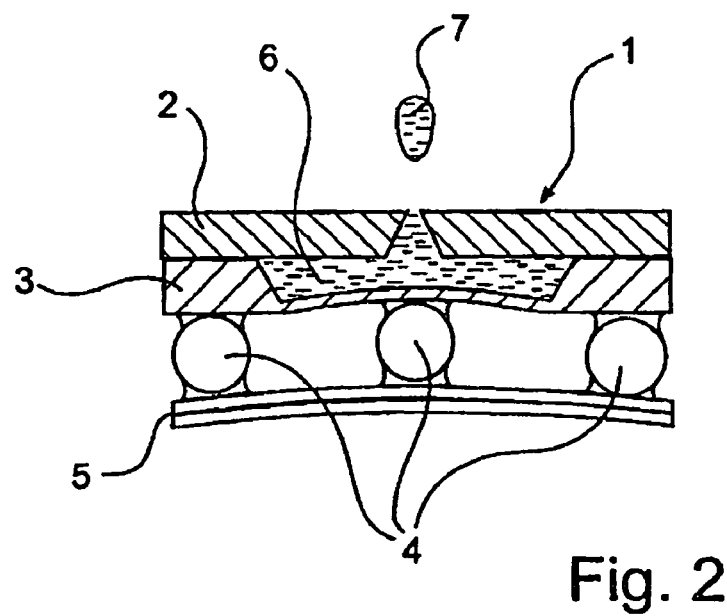
Figure 3:
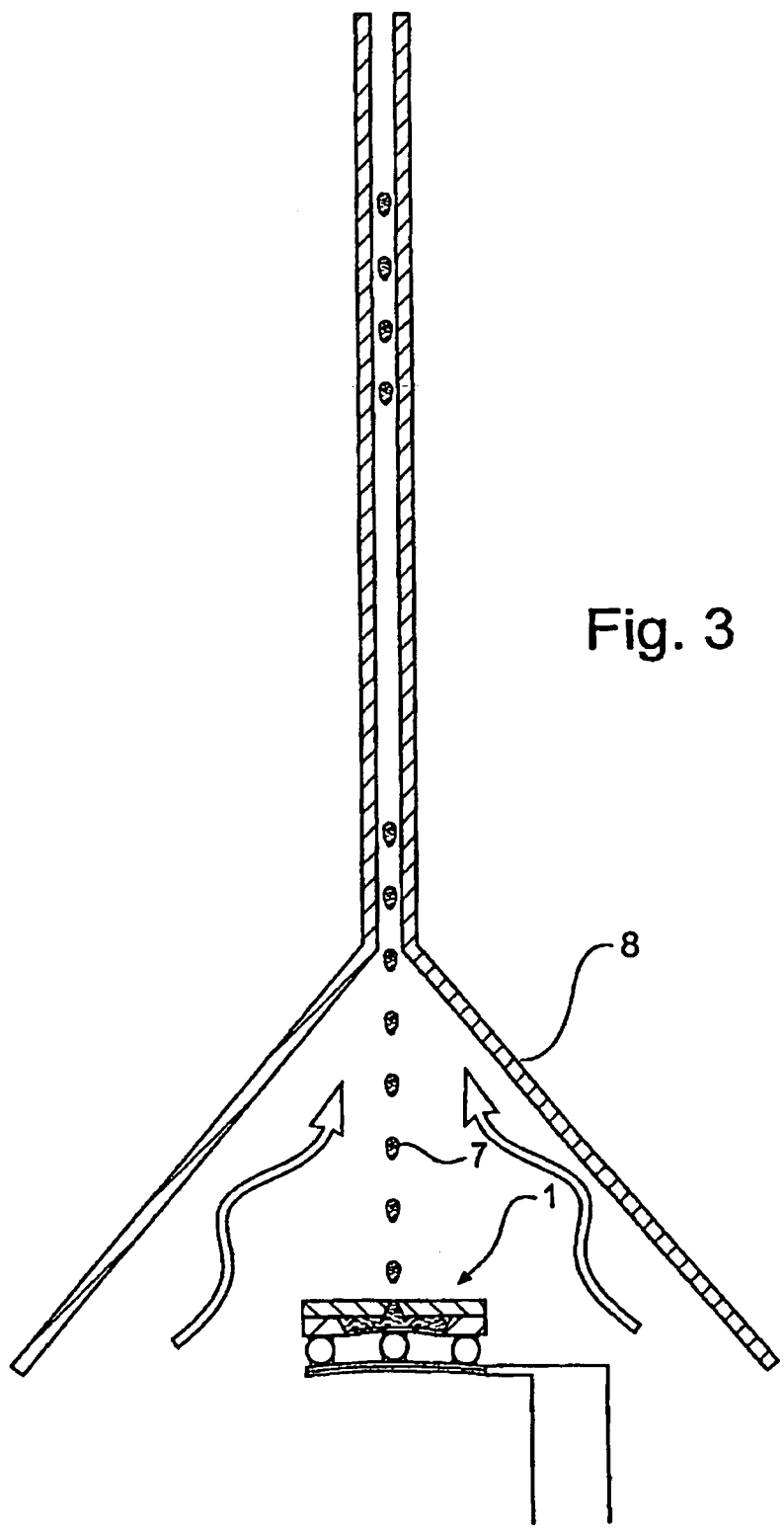
Figure 4:
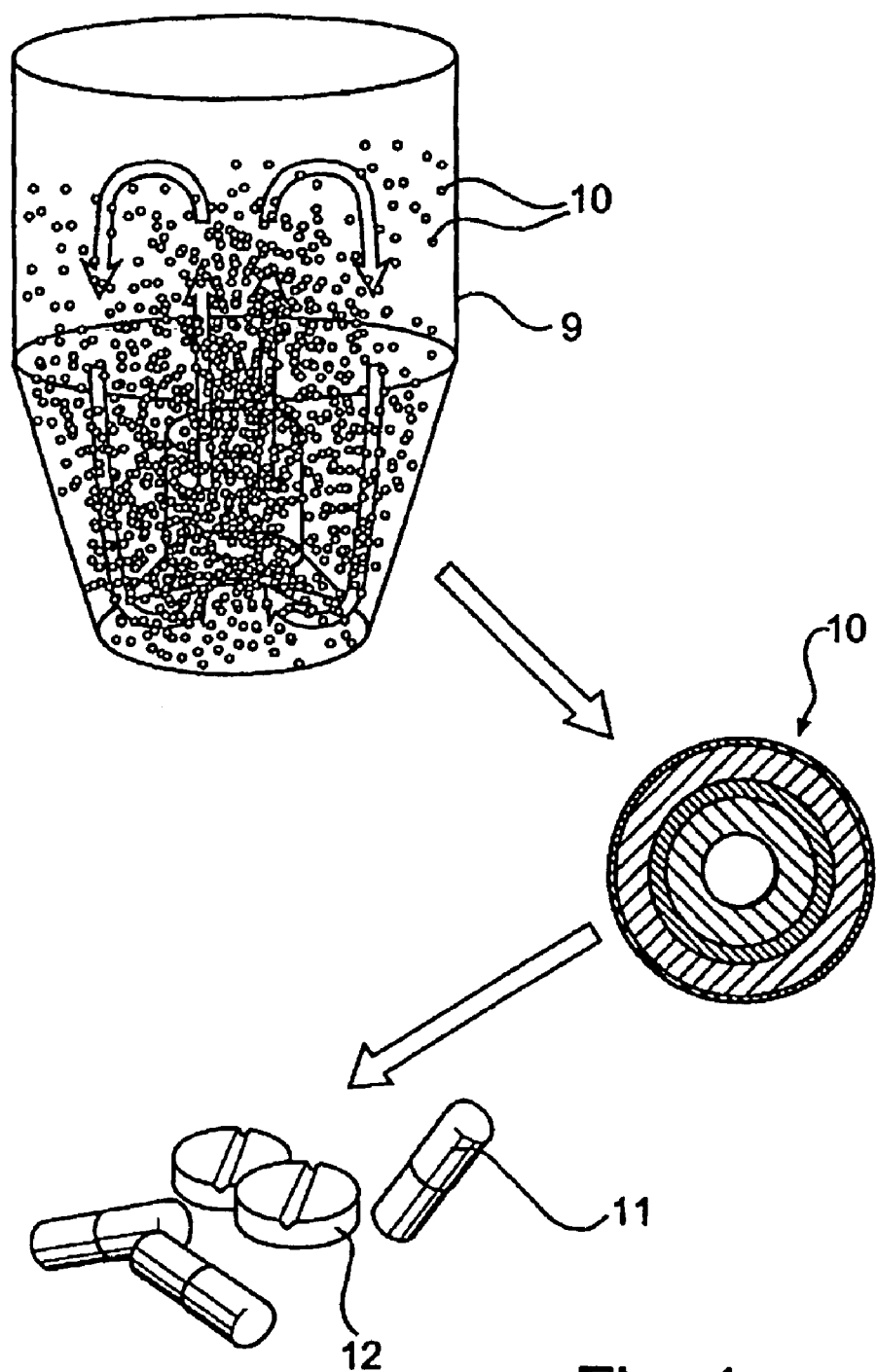
Figure 5:
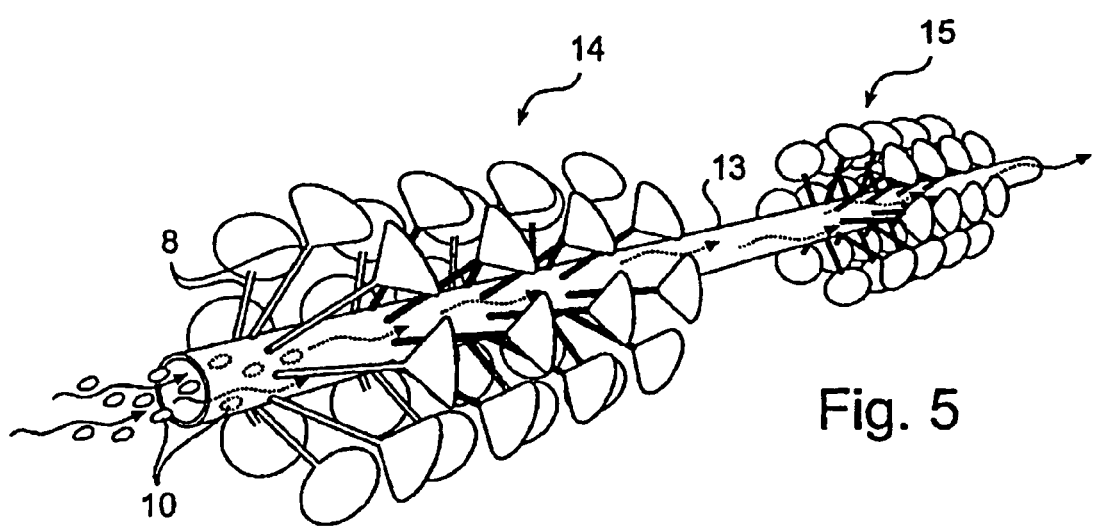

| | | | |
|---|---|---|---|
| 6,063,194 A | * | 5/2000 | Poliniak et al. .............. 118/623 |
| 6,156,120 A | * | 12/2000 | Heffels et al. ................. 118/56 |
| 6,220,075 B1 | | 4/2001 | Papen et al. |
| 6,946,157 B2 | | 9/2005 | Folestad et al. ........... 427/2.15 |

FOREIGN PATENT DOCUMENTS

| | | |
|---|---|---|
| EP | 0 505 319 A2 | 9/1992 |
| EP | 0 505 319 A3 | 9/1992 |
| EP | 0 574 173 A1 | 12/1993 |
| WO | WO93/00991 | 1/1993 |
| WO | WO01/51915 | 7/2001 |

OTHER PUBLICATIONS

Bergkvist et al, Micro Total Analysis Systems, pp. 147-148, 2001.*

Laurell et al., "Design and development of a silicon microfabricated flow-through dispenser for on-line picolitre sample handling", J. Micromech. Microeng. 9 (1999) 369-376.

Letter from Mexican Law Firm dated Mar. 29, 2006 [discussing AD, below].

Mexican Office Action dated Apr. 12, 2006 [citing WO 01/51915, cited by Applicants in an IDS filed Jan. 27, 2004, which is related to Ref. AA (U.S. Patent 6,946,157) above].

* cited by examiner

METHOD AND DEVICE FOR COATING PHARMACEUTICAL PRODUCTS

CROSS-REFERENCE TO RELATED APPLICATIONS

This application is the national phase application under 35 U.S.C. § 371 of PCT International Application No. PCT/GB02/03143, which has an International filing date of Jul. 9, 2002, and which designated Swedish Application Serial No. 0102511-3, filed Jul. 12, 2001, as priority. The contents of these applications are incorporated by reference in their entirety.

FIELD OF THE INVENTION

The present invention relates to a method and device for coating of a pharmaceutical product. Essentially, the invention relates to producing coating droplets of controlled size, shape and composition and with controlled velocity.

BACKGROUND OF THE INVENTION

The production of pharmaceutical solid dosage forms involves a multistage operation. It requires between six and eight unit processes, such as charging of raw materials, milling, granulation, drying, blending, compression, coating and packaging. Generally, a coating of a pharmaceutical product consists of one or more films and each film consists of one or more layers. From here and on "coating" is used as a comprehensive expression encompassing everything from an individual layer to a combination of several different films. Each film is the result of a single coating step, generally carried out in a coating vessel where, for instance, layers of the film are built up. The coating process takes place either in a fluidised bed wherein particles, so-called nuclei, are sprayed with a specific coating liquid, or by passing the particles through a spray dust of said liquid. Several other generally used coating techniques are known in the prior art, such as melting, aggregation etc. The total process of manufacturing a complete coating may involve a plurality of such coating steps. However, the process may as well be sequential, whereby the whole process represents a continuous flow.

Pharmaceutical products are coated for several reasons. A protective coating normally protects the active ingredients from possible negative influences from the environment, such as for example light and moisture but also temperature and vibrations. By applying such a coating, the active substance is protected during storage and transport. A coating could also be applied to make the product easier to swallow, to provide it with a pleasant taste or for identification of the product. Further, coatings are applied which perform a pharmaceutical function such as conferring enteric and/or controlled release. The purpose of functional coating is to provide a pharmaceutical preparation or formulation with desired properties to enable the transport of the active pharmaceutical substance through the digestive system to the region where it is to be released and/or absorbed. A desired concentration profile over time of the active substance in the body may be obtained by such a controlled course of release. An enteric coating is used to protect the product from disintegration in the acid environment of the stomach. Moreover, it is important that the desired functionalities are constant over time, i.e., during storage. By controlling the quality of the coating, the desired functionalities of the final product may also be controlled.

There are strict requirements on pharmaceutical products. These requirements will put high demands on the quality of the coating and require that the complex properties of the coating will be kept within narrow limits. In order to meet these demands, there is need for accurate control of the coating process.

The quality of the coating depends on physical and/or chemical properties of the coating, such as chemical composition, local inhomogeneities, physical and chemical homogeneity, density, mechanical properties, static parameters, modulus, tensile strength, elongation at break, compression, ductility, viscoelastic parameters, morphology, macro- and microscopic properties, amorphous and/or crystallinity, permeability, porosity, aggregation, wettability, degree of coalescence/maturity, stability and ability to resist chemical and/or physical degradation. There are also other properties not listed above. The quality of the coating affects to a great extent the release properties and has a significant impact on the storage stability. In order to keep the quality of the coating within the desired narrow limits it is necessary to control the manufacturing process of the coating accurately.

In an industrial plant for coating pharmaceutical products, selected process parameters are monitored and controlled to achieve a desired quality of the end product. Such process parameters are generally global and could include, for example, the pressure in the coating vessel, the flow rate and temperature of gas and coating liquid supplied to the coating vessel, etc. However, the influence of such global process parameters on the coating process, and ultimately on the coating properties of the end product, is known only from experience in a specific plant. Thus, a processing scheme is developed for each specific plant by extensive testing. When, for example, the size or shape of the coating vessel is changed during scaling up of the process the local environment of the particle may be altered. This calls for time-consuming measurements and adjustments in order to regain the same coating properties of the end product.

There is also a need to improve existing-manufacturing processes as well as to improve existing plants. Today, this is a laborious task since the influence of any change in the process scheme or the plant design on the end product has to be investigated by extensive testing, often in full scale. The same applies to the development of new products, for example when a new type of particle or coating liquid should be used.

An attempt to fulfil the above-identified needs is disclosed in the article "Fluidized bed spray granulation, investigation of the coating process on a single sphere" by K. C. Link and E. U. Schlünder, published in Chemical Engineering and Processing, No. 36, 1997. A laboratory-scale apparatus is designed for analysis of a single particle in order to investigate the fundamental physical mechanisms that lead to particle growth by layering. In this apparatus, a single aluminium sphere is made to levitate on a fluidising airflow, which is supplied by a capillary tube. Thereby, the sphere is freely and rotatably suspended at a stable location in a coating vessel. An ultrasonic nozzle arranged above this stable location is intermittently activated to generate a spray dust of coating liquid that falls down onto the sphere and forms a coating thereon. This type of nozzle generates a spray of droplets, the velocity of which is adjusted by means of a separate airflow through the nozzle. The apparatus is used for investigating the influence of different parameters, such as droplet velocity, temperature of fluidising air, drying time, and type of coating liquid, on the thickness and morphology of the resulting coating. A rough measurement value of the overall thickness of the coating is obtained by weighing the sphere before and after the actual coating process and determining the difference in weight. The morphology of the coating is qualitatively examined by arranging the sphere, once coated, in a scanning-electron-microscope (SEM). For both these measurements, the sphere must be removed from the apparatus for analysis. The apparatus also includes a lamp for illumination of the sphere and a video camera for continuous and qualitative observation of the contours of the sphere during the coating process. One drawback of this prior art apparatus resides in the difficulty to make quantitative, time-resolved measurements of coating properties. After a specific time period, the coating process must be interrupted for analysis of the coating on the sphere, whereupon a new and non-coated sphere must be subjected to a new coating process for a longer time period, and so on. In this approach, the formation of a coherent time series of measurement data requires that identical conditions be maintained in the environment of each sphere. Thus, the coating process must be repeated in exactly the same manner for each sphere. This is difficult. For example, any small variation in the masses of the aluminium spheres will necessitate an adjustment in the flow rate of the fluidising air to maintain each sphere at the same location in the vessel. Such a change in flow rate will also change the environment of the sphere during the coating process, thereby making it difficult to compile the measurement data from several consecutive measurements into coherent time series.

A further drawback of this known apparatus is that only a few properties of the coating, i.e. average thickness and surface morphology, can be measured.

Another drawback is that the course of coating process can only be studied on standardised spheres, so that the coating process can be repeated in exactly the same manner for each sphere. However, the coating process is believed to be highly dependent on the properties of the particle itself, such as the size, density, porosity and shape of the particle. Thus, it may be difficult, or even impossible, to draw any conclusions for a realistic particle from experiments made in the known apparatus.

In a paper by S. Watano and K. Miyanami, "Control of Granulation Process by Fuzzy Logic", North American Fuzzy Information, 1999, $18^{th}$ International Conference of the NAFIPS, pp 905-908, a system for granulation is described. A system has been developed for on-line monitoring of granule growth in fluidised bed granulation utilising bed granulation. However, since an image analysis is carried out the data available is limited to size and shape.

The papers above describe systems for monitoring the coating and granulation, respectively. However, the production of droplets is relatively rough and the repeatability of droplet size, velocity and direction is inadequate. Also, in a coating process it is desirable that the droplets produced hit and impinge the particles subjected to coating.

A paper by T. Laurell et al., "Design and development of a silicon microfabricated flow-through dispenser for on-line picoliter sample handling", Journal of Micromechanical Microengineering, No. 9, 1999, pp 369-376, discloses a method for producing droplets with high repeatability as regards size. However, at a coating process in for example a fluidised bed, the gas/air in the vessel is circulated and thereby carries the droplets that, if the process is properly adjusted, hit the particles subjected to coating. A major drawback is that the droplets have approximately the same velocity as the particles subjected to coating and the time of flight for the droplets are therefore often to long. This results in the droplets drying and very often not at all impinging on the particles subjected to coating. Generally the droplets consists of substances that are costly and therefore it is desirable to keep production loss down.

SUMMARY OF THE INVENTION

The object of the present invention is to solve or alleviate some or all of the problems described above. This object is achieved with a method and a device according to claim 1 and claim 15, respectively. Preferred embodiments of the invention are given by the depending claims.

Thus, the method according to the invention for coating of a pharmaceutical product, comprises the steps of producing discrete droplets of controlled size, shape and composition with a micro dispenser, controlling the production frequency and modulation of the droplets, distributing droplets with controlled velocity and time of flight, controlling the flow rate, temperature and composition of the carrier gas, and directing droplets towards particles subjected to coating. The inventive method will allow for production of droplets of controlled size, shape and composition and not dependent on the airflow in, for example, a vessel for a fluidised bed. Normally in a fluidised bed, the particles to be subjected to coating are circulated in the vessel by a jet stream, said jet stream also shattering a coating liquid and thereby producing droplets. If the system is well tuned the droplets hit the particles immediately after they leave the jet nozzle. However, since the flow circulating the particles in the vessel are directly dependent on the flow in the jet stream, the scale up from test rigs to running production units are very laborious and very often fail. With the inventive method the release of droplets is carried out independent of said flow. By using a separate gas flow to accelerate the droplets the velocity can also be determined independent of the flow inside, for example, a vessel or a pipe. This separate gas flow or carrier gas can be controlled as regards flow rate, temperature and composition. Further, the production frequency and modulation of droplets are controlled in order to increase the coating quality.

By controlling the flow rate of the carrier gas the velocity of the droplets can be controlled to be higher than the flow in the vessel or pipe. Being able to control the temperature and composition of the carrier gas can facilitate the coating using specific coating substances, i.e. avoiding for example chemical reactions and drying out of the substance. Also, by directing the droplets the loss of coating substance can be kept at a minimum.

The production of droplets is preferably carried out utilising a piezo-actuated micro dispenser. The piezo-actuated micro dispenser has the advantages of a relatively simple construction, and thereby economically beneficial, and very low standard deviations in size, shape and composition of the droplets.

As previously mentioned a separate gas can be used to carry the droplets. To further improve the accuracy of aim of the droplets a hollow cone is preferably used, or a device with corresponding flow profile, which enhance the controllability of the direction of the droplets. Due to the flow field in the cone the droplets will be forced to enter the capillary in the top of the cone. The shape of the velocity profile in the gas stream inside the capillary contributes to force droplets from impinging the wall of the capillary (Saffman force). By changing the flow rate of the carrier gas the velocity of the droplets when they impinge on the particles subjected to coating can be varied and hence the momentum of the droplets when they impinge on the particles subjected to coating can be varied. Common problems in coating in prior art is the occurrence of drying before the droplets impinge on the particles subjected to coating and not being able to direct the droplets towards the particles, which leads to a decrease in coating efficiency and also a non-optimal coating situation. By controlling the temperature and composition of the carrier gas, the drying rate of the droplets can be held at a minimum level.

Preferably, the micro dispenser is mounted in the centre of the base of said hollow cone. Due to the flow field in the cone the droplets will be forced to enter the capillary in the top of the cone.

The coating method is preferably utilised in a fluidised bed or for continuous coating in a pipe/tube, whereby several "cones" comprising micro dispensers are positioned in or adjacent to the bed or the pipe/tube. However, it is possible to utilise the method according to the present invention with coating techniques such as in a fluidised bed with top spray, with a rotor tangential spray coater and in a coating pan.

In order improve the result of the coating the coating and droplet production is preferably monitored. The monitoring can be carried out performing spectrometric measurements and preferably continuous. The spectrometric measurement can be performed by means of a spectrometric method based on any part of the electromagnetic spectrum. Another possibility is to perform the spectrometric measurement by means of imaging spectrometry. If the monitoring is carried out continuously, the output from these measurements can be used as input signals to the droplet production unit and thereby maximise the efficiency of the coating.

A device for coating of a pharmaceutical product according to the present invention comprises a piezo-actuated micro dispenser as droplet producing unit in order to produce droplets with controlled size, shape and composition. The droplet-directing unit comprises a hollow cone in which a carrier gas is made to flow and to transport the droplets produced by the micro dispenser.

Several devices such as said device could be arranged in one-, two- or three-dimensional arrays, wherein each of the devices is separately controlled. Such multiple unit systems could be used in order to have different coating zones in for example a fluidised bed coating process or in a continuous coating process where several coating zones can be arranged along the flow path of the particles.

BRIEF DESCRIPTION OF DRAWINGS

The above and other features and advantages of the invention are defined in the claims and described in greater detail below with reference to the accompanying drawings, which illustrate preferred embodiments.

FIG. 1 is a cross-sectional view of a piezo-actuated micro dispenser according to the present invention.

FIG. 2 is a cross-sectional view of a piezo-actuated micro dispenser with droplet substance according to the present invention.

FIG. 3 is a side view of a micro dispenser and a hollow cone according to the present invention.

FIG. 4 shows some steps in the production of a coated article for pharmaceutical products.

FIG. 5 shows an array of droplet directing units arranged adjacent a pipe.

DESCRIPTION OF PREFERRED EMBODIMENTS

The micro-dispenser 1 in FIG. 1 according to the present invention comprises a first silicone structure 2 with an orifice joined together with a second silicone structure 3. The two silicone structures 2 and 3 form a flow-through channel for a substance 6 (shown in FIG. 2) to be used as a coating for the particles. In a preferred embodiment of the present invention the two silicone structures, 2 and 3, rest upon Plexiglas® stands 4. The micro-dispenser 1 is actuated through a piezo-ceramic plate 5. The generation of the pressure wave is less efficient when attaching the piezo-ceramic plate directly to the silicone structure 3 than when mounting the piezo-ceramic plate 5 on Plexiglas® stands 4.

FIG. 2 illustrates the micro-dispenser 1 when actuated by the piezo-ceramic plate 5. The second said silicone structure 3 is bent inwards as a result of the voltage applied on the piezo-ceramic plate 5. As a result thereby a droplet 7 of coating substance 6 is produced and squeezed out through the orifice in said first silicone structure 2.

The micro-dispenser 1 is in a preferred embodiment of the present invention arranged in the centre of the base of a hollow cone 8, which is illustrated in FIG. 3. A carrier gas is supplied around the micro-dispenser in an upward direction in order to carry the droplets 7. By changing the flow rate of the carrier gas the velocity of the droplets 7 can be varied. Due to the flow field in the hollow cone 8 the droplets will be forced to enter the capillary in the top of the cone. Due to the velocity profile inside the capillary the Saffman force prevents the droplets 7 from impinging the wall of the capillary. The carrier gas is preferably adapted to the substance of the droplets 7. By controlling the temperature and composition of the carrier gas, the drying rate can be adjusted to create optimal drying conditions for a certain coating quality.

Referring to FIG. 4, the coating device shown in FIG. 3 is preferably arranged in a fluidised vessel 9. Particles 10 subjected to coating are made to flow in the fluidised vessel 9, for example using a jet nozzle (the coating device and jet nozzle are not shown in FIG. 4).

In a preferred embodiment of the present invention several devices (not shown in FIG. 4) similar to the one shown in FIG. 3 are arranged in the vessel 9. By arranging monitoring equipment (not shown) the coating layers of the particles 10 subjected to coating as well as the droplet generation can be analysed and an algorithm decides when the micro dispensers 1 are to produce droplets and their properties. Also, said devices are positioned as desired according to the results of the monitoring.

In a further preferred embodiment of the present invention several devices similar to the one shown in FIG. 3 are arranged to coat particles continuously in a pipe/tube. Also with this arrangement it is possible to monitor the coating and thereby achieve information in order to maximise the quality of the coating.

The supply of carrier gas in the device shown in FIG. 3 is preferably independent of the gas flow inside the vessel 9. One advantage with this is that the droplets 7 can be accelerated to have a higher velocity than the particles 10 subjected to coating in the vessel. This will in turn increase the fraction of droplets 7 hitting the particles 10 subjected to coating. When the coating is completed the pharmaceutical particles 10 can for example be put in capsules II or mixed with filler and compressed to tablets 12.

FIG. 5 shows a continuous coating process according to the present invention. Particles 10 subjected to coating are transported in a pipe/tube 13, said pipe/tube 13 being equipped with coating devices 8. The coating devices 8 are arranged in several arrays 14, 15, each of the arrays correspond to one layer of coating. The arrangement of the coating devices 8, such as angles, spacing and number, within the arrays 14, 15 are varied to maximise the coating quality.

The foregoing is a disclosure of preferred embodiments for practising the present invention. However, it is apparent that device and method incorporating modifications and variations will be obvious to one skilled in the art. Inasmuch as the foregoing disclosure is intended to enable one skilled in the art to practice the instant invention, it should not be construed to be limited thereby, but should be construed to include such modifications and variations as fall within its true spirit and scope.

The invention claimed is:

1. A method of coating particles of a pharmaceutical product inside a vessel or a pipe, comprising the following steps:
   producing discrete droplets with at least one micro dispenser;
   controlling the flow rate, temperature and composition of a carrier gas flowing from a supply to a droplet directing unit;
   causing the particles to flow in the vessel or pipe;
   using the carrier gas, directing droplets through the droplet directing unit towards the particles in the vessel or pipe; and
   coating the particles with the droplets;
   wherein the supply of the carrier gas is independent of the flow of particles inside the vessel or pipe such that the droplets are accelerated to have a higher velocity than the particles.

2. A method as set forth in claim 1, wherein the production of the discrete droplets is carried out using a piezo-actuated micro dispenser.

3. A method as set forth in claim 1, wherein the droplets are accelerated by the carrier gas.

4. A method as set forth in claim 1, further comprising adjusting the velocity of the droplets by varying the flow rate of the carrier gas.

5. A method as set forth in claim 1, wherein die droplet directing unit comprises a hollow cone.

6. A method as set forth in claim 5, wherein the hollow cone surrounds the micro dispenser.

7. A method as set forth in claim 1, wherein the coating is performed in a fluidised bed.

8. A method as set forth in claim 1, wherein the coating is performed continuously in a pipe, in which said pharmaceutical product is transported by a carrier gas.

9. A method as set forth in claim 7, wherein the formation of the coated pharmaceutical product is monitored.

10. A method as set forth in claim 9, wherein the monitoring is carried out performing spectrometric measurement.

11. A method as set forth in claim 10, wherein said spectrometric measurement is carried out continuously.

12. A method as set forth in claim 10, wherein said spectrometric measurement is performed by means of spectrometric method based on any part of the electromagnetic spectrum.

13. A method as set forth in claim 10, wherein said spectrometric measurement is performed by means of imaging spectrometry.

14. A method as set forth in claim 9, wherein the output from said monitoring is used as input to control the distribution of the droplets.

15. A device for coating particles of a pharmaceutical product inside a vessel or a pipe in which the particles flow, the device comprising a droplet producing unit, a droplet directing unit, the droplet producing unit comprising a piezo-actuated micro dispenser configured to produce discrete droplets, and a supply of a carrier gas provided for transporting droplets through said droplet-directing unit to coat said particles, the supply of carrier gas being independent of the flow of particles inside the vessel or pipe such that the droplets are accelerated to have a higher velocity than the particles.

16. A device as set forth in claim 15, wherein the piezo-actuated micro dispenser comprises a piezo-ceramic element.

17. A device as set forth in claim 15, wherein the micro-dispenser comprises two joined silicone structures forming a flow-through channel.

18. A device as set forth in claim 16, wherein stands are provided between said micro dispenser and said piezo-ceramic element, spacing the micro dispenser from the piezo-ceramic element.

19. A device as set forth in claim 17, wherein said flow-through channel comprises an orifice.

20. A device as set forth in claim 15, wherein the device comprises an array of droplet producing units and droplet directing units.

21. A device as set forth in claim 20, wherein each droplet producing unit is separately controlled.

22. A device as set forth in claim 20, wherein several arrays are arranged in a coating device selected from the group consisting of fluidized beds, fluidized vessels, pipes, tubes, fluidized beds with a top spray, rotor tangential spray coaters, and coating pans to provide different coating zones in the coating device.

23. A device as set forth in claim 22, wherein the coating device comprises a fluidised bed.

24. A device as set forth in claim 22, further comprising a pipe or tube configured for continuous coating.

* * * * *